United States Patent [19]
Brockhaus

[11] 3,954,857
[45] May 4, 1976

[54] PROCESS FOR PREPARING ACETIC ACID BY GAS-PHASE OXIDATION

[75] Inventor: Rudolf Brockhaus, Marl, Germany

[73] Assignee: Chemische Werke Huls Aktiengesellschaft

[22] Filed: Oct. 18, 1974

[21] Appl. No.: 515,967

[30] Foreign Application Priority Data
Oct. 31, 1973 Germany............................ 2354425

[52] U.S. Cl.......................... 260/533 R; 260/497 A; 260/530 N; 260/533 N
[51] Int. Cl.².......................................... C07C 51/20
[58] Field of Search........ 260/533 R, 497 A, 530 N, 260/533 N

[56] References Cited
FOREIGN PATENTS OR APPLICATIONS
2,016,681 10/1971 Germany.......................... 260/533 R

*Primary Examiner*—Anton H. Sutto
*Attorney, Agent, or Firm*—Gilbert L. Wells

[57] ABSTRACT

Vanadate catalysts used in the preparation of acetic acid by gas-phase oxidation of butenes and of oxygen compounds derived from butene or from propane in the presence of steam are improved by treating with hydrochloric acid, following calcining, and then washing, drying and calcining a second time.

4 Claims, No Drawings

PROCESS FOR PREPARING ACETIC ACID BY GAS-PHASE OXIDATION

CROSS-REFERENCE TO A RELATED APPLICATION

Applicant claims priority under 35 U.S.C. 119 for Application P 23 54 425.4,filed Oct. 31, 1973 in the Patent Office of the Federal Republic of Germany.

BACKGROUND OF THE INVENTION

The invention relates to a process for preparing acetic acid by the gas-phase oxidation of butenes and of oxygen compounds derived from butene or propene by means of gases containing oxygen or by meas of oxygen, at elevated temperatures and in the presence of vanadate catalysts contaning steam or water vapor. These catalysts are of improved selectivity and can be mounted with or without an inert carrier substance.

The state of the art of acetic acid production and vanadate catalysts useful therein may be ascertained by reference to Kirk-Othmer "Encyclopedia of Chemical Technology," 2nd Edition, Vol. 8 (1966) pp. 386–404 under the section Ethanoic Acid, particularly pages 393–398 wherein synthetic methods are disclosed; Vol. 21 (1970), pp. 171–173 wherein vanadium oxides and vanadates are disclosed; U.S. Pat. Nos. 3,431,297; 3,439,029; 3,459,797 and 3,627,823 of Rudolf Brockhaus; West German Pat. Nos. 1,269,119 and 2,026,744; West German Published Applications No. 2,016,681 (abstracted in Chemical Abstracts at Vol. 76, p. 13835 v) and 2,164,023 the disclosures of which are incorporated herein.

It is known that acetic acid may be prepared by gas-phase oxidation in the presence of catalysts containing mixed oxides of vanadium (vanadates) with, for instance, titanium, tin, antimony, aluminum, silicon, zirconium or molybdenum and tungsten as disclosed in West German patent Nos. 1,269,119 and 2,026,744; West German Published Application 2,164,023; U.S. Pat. Nos. 3,431,297 and 3,459,797. A titanium-vanadium mixed oxide catalyst is a particularly suitable catalyst. The butenes are oxidized in the presence of the cited catalysts in the presence of steam and at elevated temperatures by means of oxygen or of gases containing oxygen.

As disclosed in U.S. Pat. No. 3,431,297 titanium and aluminum vanadate catalysts are produced starting with a solution of vanadium pentoxide and titanium tetrachloride and/or aluminum trichloride in strong hydrochloric acid. Upon neutralization of the hydrogen ions, a mixed oxide is obtained which precipitates. This mixed oxide is designated titanium and/or aluminum vanadate. In the catalysts of U.S. Pat. No. 3,431,297 which are ready to be used, the atomic ratio of titanium and/or aluminum to vanadium is 10:1 to 1:10, preferably 1:05 to 1:2, and therefore include ortho, pyro and meta-vanadates, especially the ortho and pyro-vanadates.

U.S. Pat. No. 3,459,797 discloses the preparation of tin vanadate catalysts for use in the process of converting oxygen and a butene into acetic acid. These tin vanadate catalysts have a molar ratio of tin to vanadium of 10:1 to 1:10, preferably 1:05 to 1:2, and therefore include ortho, pyro and meta vanadates.

According to U.S. Pat. No. 3,439,029 antimony vanadate catalysts are employed in the gas-phase oxidation of butene to acetic acid wherein the atomic ratio of antimony to vanadium is desirably 1:3 to 2:1, preferably 0.9:1 to 1:1.5.

As disclosed in U.S. Pat. No. 3,627,823, oxygen compounds derived from butene or propene, for instance secondary-, tertiary- and isobutanol, isobutyraldehyde, isobutyric acid, acetone and methylethylketone are also used as raw materials for the process of preparing acetic acid wherein the catalysts are vanadates of tin, antimony, titanium and aluminum.

West German Published Application No. 2,016,681 (Rudolf Brockhaus et al, abstracted in Chemical Abstracts, Vol. 76, p. 13835v) discloses that catalysts made from the mixed oxides of vanadium (vanadates) with tin, antimony, titanium and aluminum or made from mixed oxides of vanadium and oxide mixtures of these metals are improved by treating hydroxide precipitates obtained in preparing the metals with an oxidizer, preferably hydrogen peroxide. Though catalysts are obtained in such a manner which allows preparing acetic acid with satisfactory yields and favorable reaction rates. These catalysts nevertheless suffer from several undesirable mechanical properties and hardness especially is unsatisfactory.

SUMMARY OF THE INVENTION

The present invention has as an object developing catalysts of high activity and selectivity for acetic acid formation, which are free of hardness impairment.

The object is achieved by the invention in that the conventionally prepared vanadate catalysts following calcination are treated with hydrochloric acid, whereupon they are washed, dried and calcined a second time in known manner.

The process of the present invention uses catalysts containing vanadium oxide, especially mixed oxides of vanadium with tin, aluminum and titanium, and also includes catalysts containing vanadium oxide and oxide mixtures of the last-mentioned metals. Especially good results are achieved with catalysts containing titanium and vanadium oxide.

These mixed oxides are designated in the following disclosure as "vanadates."

The vanadate catalysts used in the present invention have an atomic ratio of other metal to vanadium of 1 : 10 to 10 : 1 , preferably 1 : 2 to 1 : 0.5.

The titanium vanadate catalyst useful in the present invention has preferably an atomic ratio of titanium to vanadium of 1 : 2 to 1 : 0.5.

The tin vanadate catalyst useful in the present invention has preferably an atomic ratio of tin to vanadium of 1 : 1.5 to 1 : 0.4.

Aluminum vanadate catalyst useful in the present invention has preferably an atomic ratio of aluminum to vanadium of 1 : 2 to 1 : 0.5.

DESCRIPTION OF THE PREFERRED EMBODIMENTS

Catalyst preparation is such that, for instance, one precipitates by means of ammonium and in common the compounds of a hydrochloric acid solution of vanadium oxide and of the particular second catalyst component and is necessary or desired in the presence of inert substances acting as carriers. These precipitates are then washed, shaped and dried and calcined at about 300°– 400°C.

The catalyst so obtained are then treated in accordance with the invention with aqueous hydrochloric acid, washed with water, and generally dried at 110°–

150°C, and then calcined in a conventional manner and generally from about 300° to 450°C.

The catalysts are used as full-contact catalysts or, if necessary or desired, in combination with carrier materials, for example diatomaceous earth or aluminum oxide, and preferably with active silica gel.

As regards the vanadate catalyst of titanium, tin or aluminum, it was found advantageous to carry out the HCl treatment of the conventionally prepared catalysts with about 15 – 35 percent hydrochloric acid for about 3 – 5 minutes and at about 40°– 80°C.

When the catalysts are treated with stronger hydrochloric acid solutions, and/or at higher temperatures, and/or for longer periods of time than previously indicated, then excessive amounts of vanadium oxide are dissolved and removed, especially as regards the tin-vanadate catalyst and the aluminum vanadate catalyst, whereby the catalyst suffers from degradation of activity and selectivity and from poorer mechanical properties. When treatment is gentler than indicated above, the optimum possible selectivity and activity is not obtained, especially with respect to the titanium vanadate catalyst.

Specific conditions are found to be particularly advantageous with respect to given hydrochloric acid treatment of particular catalysts. Thus, as regards the conventionally prepared titanium vanadate catalyst, treatment is from about 5 to 30 minutes at about 50° to 80°C temperature and with about 15 to 35 percent hydrochloric acid.

Treatment of the aluminum vanadate catalyst is especially advantageous when carried out for about 5 – 30 minutes at about 40° – 60°C and with about 15 – 20 percent hydrochloric acid.

In the case of a tin-vanadate catalyst, gentler treatment than for the aluminum vanadate catalyst suffices for improving the catalytic activity and preferably the catalyst is treated about 5 – 15 minutes at about 40°– 50°C with about 15 – 20 percent hydrochloric acid.

In contrast to treatment by an oxidizer (West German Published Application No. 2,106,681), the mechanical hardness of the catalysts is not affected by treatment with hydrochloric acid. The initial hardness of the non-treated catalyst is kept as long as the treatment conditions listed above are followed. The catalyst is slightly etched in the treatment with the hydrochloric acid, so that a slight amount of catalyst is dissolved and removed, whereby there is a slight change in the ratio of vanadium oxide to the particular second oxide present. An enlargement of the average pore volume takes place, which is determined by means of the mercury porosimeter and the specific surface in the Emmet and Teller method (Journal of the American Chemical Soc., 60, (1938), page 309). These effects establish the higher catalytic activity in the catalysts of the present invention.

The catalysts prepared in accordance with the present invention facilitate the manufacture of butenes and oxygen compounds derived from butene or propene, for instance the secondary-, tertiary-and isobutanol, isobutyraldehyde, isobutyric acid, acetone and methylethylketone of U.S. Pat. No. 3,627,823, into acetic acid by means of oxidation. Oxygen, or gases containing oxygen, preferably air, are used as oxidizing means. Steam or water vapor is added in a manner known to the prior art to the initial mixture, and preferably, an air-steam mixture is added. The required amount of steam is largely independent of pressure but the feed of hydrocarbon compounds and air however may be increased with increasing pressure. The gaseous mixture being applied and consisting of the raw materials, oxidizing gas and steam, may be varied within the ignition limits. Lowering the proportion of steam while maintaining the other conditions constant may lower the selectivity of the catalyst with respect to the formation of acetic acid. The dwell time at the catalyst should be from about 0.5 to 10 seconds, preferably from about 1 to 3 seconds. The gas-phase oxidation reaction temperature is kept between about 180° and 400°C. In the case of vanadates of titanium, aluminum or tin, the preferred gas-phase oxidation temperatures are from about 235° to 305° C. Optimum conditions may be lowered by about 20° – 40°C by means of the method of the present invention with respect to the non-treated prior art catalyst.

To increase the space time yield, it is preferred, though not absolutely necessary, to conduct the gas-phase oxidation reaction at superatmospheric pressure of 0.5 – 21, advantageously 13 – 21 atmospheres.

The prior art catalysts of U.S. Pat. Nos. 3,431,297; 3,439,029; 3,459,797; 3,627,823; West German Pat. No. 2,026,744; West German Published Application No. 2,016,681 are treated with hydrochloric acid in simple manner in the process of the present invention. This treatment provides catalysts allowing large yields and large space-time yields in the manufacture of acetic acid in surprising and unforeseeable manner, while keeping good mechanical catalysts properties, especially hardness. Simultaneously the optimum values of temperaure and pressure are lowered in the process of the present invention with respect to the state of the art.

Without further elaboration, it is believed that one skilled in the art can, using the preceding description, utilize the present invention to its fullest extent.

The examples described below serve to further explain the invention without thereby limiting it. The physical and chemical data listed in Table 1 shows the changes in the vanadate catalysts due to hydrochloric acid treatment. Table 2 lists the catalytic properties of the vanadate catalysts with and without hydrochloric acid treatment.

EXAMPLES OF CATALYST PREPARATION

EXAMPLE 1

TITANIUM VANADATE CATALYSTS (prepared conventionally)

39 liters of hydrochloric acid solution (37%); 21 liters of water and 8.2 kg of vanadium pentoxide are mixed with stirring. 17.1 kg of titanium tetrachloride are added at 10° – 20°C with cooling into the suspension. Following this addition, stirring proceeds at 60°C until the vanadium pentoxide is completely dissolved. Dissolving under heat generates chlorine and four-valent vanadium ions. Prior to precipitation the solution is cooled to about 20°C. Precipitation is carried out in cascade, consisting of 4 stirred flasks each holding 6 liters. The hydrochloric acid solution of above and 8 percent ammonium solution are introduced into flask 1 while strongly cooling. The amounts supplied are so controlled that a temperature of 60°C and a pH value of 1.5 – 2.0 is obtained in the flask. Flask 2 is used for follow-up stirring. A pH value of 5.7 is adjusted in flask 3 by adding 8 percent ammonium solution. Flask 4 also is used for follow-up stirring. Average dwell time is about 5 minutes in each flask. The dark brown precipitate is evacuated by suction, washed with water, dried at 90°C, shaped and calcined at 400°C. Time of calcining is 16 hours. The atomic proportion of titanium: vanadium is 1: 0.94.

EXAMPLE 2

TITANIUM VANADATE CATALYST (prepared by using an oxidizing means)

Part of the washed precipitate obtained in Example 1 is stirred into a paste and 15 percent hydrogen peroxide is added until the precipitate color becomes light gray. The temperature increases in this treatment and when required, is kept below 50°C by means of ice addition. The pH value drops because of oxidation and is restored to 4 by adding ammonium. Then the precipitate is removed by suction, washed with water and processed into a useful catalyst in the manner described above.

EXAMPLE 3

TITANIUM VANADATE CATALYST (prepared per invention/hydrochloric acid treatment)

In order to achieve the catalyst of the present invention, the calcined catalysts described in Example 1 is treated with 35 percent hydrochloric acid at 80°C for 10 minutes. This is followed by careful washing with $H_2O$ until the pH value rises to 4 – 5 and by drying in a vacuum at 150°C (1 percent residual humidity). Thereupon the catalyst is heated from about 250° to 400°C at the rate of 25°C an hour under nitrogen ventilation of 0.5 cubic meters per liter of catalyst and per hour, and kept under these conditions for one hour. Gas feed is switched to air feed and calcination takes place for one hour in an air atmosphere. Towards the end of calcining the effluent gas is acid-free.

EXAMPLE 4

ALUMINUM VANADATE CATALYST (prepared conventionally)

1500 gm of $Al(NO_3)_2 \cdot 9H_2O$ and 364 gm of vanadium pentoxide are dissolved in 7 liters of concentrated hydrochloric acid. The solution is reacted with 7.5 percent ammonia water in the cascade described in Example 1. Precipitation takes place. COnditions are as follows:

|  | Temperature °C | pH value |
|---|---|---|
| flask 1 | 55 | 2 |
| flask 2 | 53 | 2 |
| flask 3 | 51 | 5.5 |
| flask 4 | 50 | 5.5 |

Time of precipitation is 20 minutes. Occasional cloggings caused by the precipitate in the flasks ae remedied by adding water. The fresh precipitate is divided into two parts. Part 1 is conventionally processed into an operational catalyst. Calcining conditions are as follows:

| duration | 16 hours |
|---|---|
| temperature | 400°C |

The atomic proportion of aluminum: vanadium in the prior art catalyst of part 1 ready for use is 1:0.96.

EXAMPLE 5

ALUMINUM VANADATE CATALYST (prepared by using an oxidizing means)

Catalyst preparation is carried out with the second part of the precipitate of Example 4. The washed precipitate is made into a pasty suspension and reacted with 480 cc of 15 percent hydrogen peroxide solution. A color change occurs from dark gray to yellow. Then the precipitate is processed according to the prior art to an operational catalyst.

EXAMPLE 6

ALUMINUM VANADATE CATALYST (prepared by hydrochloric acid treatment in conformity with the present invention)

The catalyst obtained in Example 4 is treated with 20 percent hydrochloric acid at 60°C for 10 minutes. Then the catalyst is carefully washed and dried at 150°C in vacuum (1 percent residual humidity). To remove the hydrochloric acid, heat treatment is carried out as in Example 3.

EXAMPLE 7

TIN VANADATE CATALYST (prepared conventionally)

1354 gm of tin chloride ($SnCl_2 \cdot 2H_2O$) and 364 gm of vanadium pentoxide are dissolved in 3 liters of hydrochloric acid (37 percent). The solution is precipitated with 9 percent ammonia water in the cascade disclosed in Example 1, wherein the 6-liter flasks are replaced by one-liter flasks. Conditions are as follows:

|  | Temperature °C | pH value |
|---|---|---|
| flask 1 | 60 – 62 | 1.5 – 2 |
| flask 2 | 60 | 1.5 – 2 |
| flask 3 | 59 | 5.5 |
| flask 4 | 58 | 5.5 |

Total precipitation time is 20 minutes. When the precipitate causes clogging in flask 1, addition of water remedies this state. The fresh precipitate is divided into two parts. The first part is processed conventionally to an operational catalyst. Calcining conditions are as follows:

| duration | 16 hours |
|---|---|
| temperature | 390°C |

The atomic proportion of tin to vanadium in the catalyst so prepared is 1:0.67.

EXAMPLE 8

TIN VANADATE CATALYST (prepared using an oxidizing means)

Catalyst preparation takes place by means of the second part of the precipitate of Example 7. The washed precipitate is made into a pasty suspension and reacted with hydrogen peroxide until the color changes from dark gray to yellow. 550 cc of 15 percent hydrogen peroxide solution are required. Then the precipitate is processed according to the prior art into an operational catalyst.

EXAMPLE 9

TIN VANADATE CATALYST (prepared with hydrochloric acid treatment in conformity with the present invention)

The calcined catalyst obtained per Example 7 is treated 10 minutes with 20 percent hydrochloric acid at 50°C. Then the catalyst is carefully washed and dried in vacuum at 150°C (1 percent residual humidity). In order to remove the hydrochloric acid, the same procedure as in Example 3 is used in the heat treatment.

EXAMPLES OF GAS-PHASE OXIDATION

The catalysts are used in a fixed-bed facility as disclosed in column 4 of U.S. Pat. No. 3,627,823. The reactor consists of a chromium-nickel steel tube 6 meters in length and 15 mm wide which is heated by means of a salt bath. The raw material gas consists of air, steam and industrial butene mixture (53 percent butene-1, 27 percent butene-2 and 19 percent n-butane), or of oxygeneous compounds such as isobutyraldehyde or acetone, and passes through the reactor and then through a condensor where the water and the crude acid are separated. The raw materials are:

(a) gas-phase oxidation of butene
- air: 500 liter/hour standard temperature and pressure
- steam: 280 liter/hour stp.
- butene mixture: 10 liter/hour stp.
- amount of catalyst: 250 milliliters Test results are shown in Table 2/1

(b) gas-phase oxidation of isobutyraldehyde and acetone
- air: 300 liter/hour stp.
- steam: 130 liter/hour stp.
- isobutyraldehyde or acetone: 14 liter/hour stp.
- amount of catalyst: 250 milliliters Test results are shown in Table 2/11

TABLE 1

| Composition Vanadate | M/V ratio | oxidized with $H_2O_2$ | Nature of catalyst Treated with HCl | hardness in kp per strand | Bulk weight kp/liter | Strand length mm | diameter | Pore volume $cm^3/g$ | Surface $m^2/g$ |
|---|---|---|---|---|---|---|---|---|---|
| Ti | 1:0.94 | no | no | 16.2 | 1.05 | 8–12 | 5.5 | 0.31 | 31.5 |
| Ti | 1:0.91 | yes | no | 14 | 0.91 | 8–12 | 5.5 | 0.49 | 63 |
| Ti | 1:0.83 | no | yes | 16 | 0.93 | 8–12 | 5.3 | 0.45 | 52 |
| Al | 1:0.96 | no | no | 11.5 | 0.65 | 8–12 | 5.7 | 0.38 | 40–41 |
| Al | 1:0.92 | yes | no | 6.5 | 0.54 | 8–12 | 5.6 | 0.53 | 65–73 |
| Al | 1:0.87 | no | yes | 11 | 0.58 | 8–12 | 5.6 | 0.51 | 59 |
| Sn | 1:0.67 | no | no | 13.5 | 1.5 | 8–12 | 5.4 | 0.22 | 34 |
| Sn | 1:0.66 | yes | no | 12 | 1.34 | 8–12 | 5.4 | 0.39 | 58–63 |
| Sn | 1:0.61 | no | yes | 13.5 | 1.38 | 8–12 | 5.2 | 0.35 | 48.5 |

TABLE 2/1

| Nature of Catalyst | | | Gas-phase oxidation | | |
|---|---|---|---|---|---|
| Vanadate | Oxidized with $H_2O_2$ | Treated with HCl | Reaction Temperature 0°C | Conversion n-butene % | Yield (with respect to conversion %) |
| Ti | no | no | 235 | 90 | 62 |
| Ti | yes | no | 190 | 90 | 68.5 |
| Ti | no | yes | 192 | 91 | 71 |
| Al | no | no | 305 | 70 | 51 |
| Al | yes | no | 260 | 70 | 57 |
| Al | no | yes | 258 | 72.5 | 57.5 |
| Sn | no | no | 240 | 70 | 65 |
| Sn | yes | no | 220 | 85 | 66 |
| Sn | no | yes | 219 | 86.5 | 67.5 |

TABLE 2/11

| Nature of catalyst | | | Gas-phase oxidation | | |
|---|---|---|---|---|---|
| Vanadate | Oxidized with $H_2O_2$ | Treated with HCl | Starting material | Reaction Temperature °C | Conversion of initial product % | Yield (referred to conversion) |
| Ti | no | no | IBA+ | 250 | 100 | 83.1 |
| Ti | yes | no | IBA | 225 | 100 | 88.5 |
| Ti | no | yes | IBA | 221 | 100 | 89.5 |
| Sn | no | no | Acetone | 245 | 96 | 77 |
| Sn | yes | no | Acetone | 210 | 99 | 86.2 |
| Sn | no | yes | Acetone | 208 | 100 | 87.5 |

+Isobutyraldehyde

I claim:

1. In a process for the production of acetic acid by the gas phase oxidation of butenes and of oxygen compounds derived from butene or from propene with oxygen containing gases in the presence of a calcined vanadate catalyst selected from the group consisting of tin vanadate, titanium vanadate, aluminum vanadate and mixtures thereof; the improvement comprising treating said calcined vanadate catalyst with hydrochloric acid, washing, drying and calcining said vanadate catalyst a second time, wherein said treating is carried out with 15 – 35 percent hydrochloric acid from 5 to 30 minutes at temperatures from 40° to 80°C.

2. The process of claim 1, wherein said vanadate catalyst is titanium vanadate and said treating is carried out with 15 – 35 percent hydrochloric acid from 5 to 30 minutes at temperatures from 50° to 80°C.

3. The process of claim 1, wherein said vanadate catalyst is aluminum vanadate and said treating is carried out with 15 – 20 percent hydrochloric acid from 5 to 30 minutes at temperatures from 40° to 60°C.

4. The process of claim 1, wherein said vanadate catalyst is tin vanadate and said treating is carried out with 15 to 20 percent hydrochloric acid from 5 to 15 minutes at temperatures from 40° to 50°C.

* * * * *